United States Patent
Mueth et al.

(10) Patent No.: US 7,355,696 B2
(45) Date of Patent: Apr. 8, 2008

(54) METHOD AND APPARATUS FOR SORTING CELLS

(75) Inventors: Daniel Mueth, Chicago, IL (US); Amy L. Anderson, Prospect Heights, IL (US); Christopher R. Knutson, Chicago, IL (US); Joseph Plewa, Park Ridge, IL (US)

(73) Assignee: Arryx, Inc, Chicago, IL (US)

( * ) Notice: Subject to any disclaimer, the term of this patent is extended or adjusted under 35 U.S.C. 154(b) by 0 days.

(21) Appl. No.: 11/046,896

(22) Filed: Feb. 1, 2005

(65) Prior Publication Data

US 2006/0170912 A1    Aug. 3, 2006

(51) Int. Cl.
*G01N 21/01* (2006.01)

(52) U.S. Cl. .................... 356/244; 356/246; 356/39; 209/3.1

(58) Field of Classification Search ............ 356/244, 356/246, 72–73, 39–40, 336–339; 250/222 PC, 250/461.2; 436/10, 63, 18; 422/82.05; 209/571, 209/576–577, 644

See application file for complete search history.

(56) References Cited

U.S. PATENT DOCUMENTS

| | | | | |
|---|---|---|---|---|
| 3,649,829 A | * | 3/1972 | Randolph | 250/364 |
| 3,960,449 A | * | 6/1976 | Carleton et al. | 356/340 |
| 4,395,397 A | * | 7/1983 | Shapiro | 424/577 |
| 4,660,971 A | * | 4/1987 | Sage et al. | 356/39 |
| 4,667,830 A | * | 5/1987 | Nozaki et al. | 209/3.1 |
| 5,007,732 A | * | 4/1991 | Ohki et al. | 356/73 |
| 5,138,181 A | * | 8/1992 | Lefevre et al. | 250/573 |
| 5,180,065 A | * | 1/1993 | Touge et al. | 209/577 |
| 5,194,909 A | * | 3/1993 | Tycko | 356/40 |
| 5,483,469 A | * | 1/1996 | Van den Engh et al. | 702/21 |
| 5,707,808 A | * | 1/1998 | Roslaniec et al. | 435/6 |
| 5,879,625 A | * | 3/1999 | Roslaniec et al. | 422/50 |
| 5,985,216 A | * | 11/1999 | Rens et al. | 422/73 |
| 6,524,860 B1 | * | 2/2003 | Seidel et al. | 436/63 |
| 2002/0176069 A1 | * | 11/2002 | Hansen et al. | 356/73 |
| 2006/0152707 A1 | * | 7/2006 | Kanda | 356/73 |

* cited by examiner

*Primary Examiner*—Sang H. Nguyen
(74) *Attorney, Agent, or Firm*—Jean C. Edwards, ESQ.; Akerman Senterfitt

(57) ABSTRACT

Apparatus for sorting and orienting sperm cells has a pair or walls in confronting relationship forming a flow chamber having inlet, a downstream outlet, and intermediate detector region. The inlet receives first and second spaced apart streams of input fluid and a third stream of sample fluid containing the cells to be sorted. The first and second streams have respective flow rates relative to third stream, such that the third stream is constricted forming a relatively narrow sample stream, so that the cells are oriented parallel to the walls. A detector detect desired cells and a sorter downstream of the detector for sorting the desired cells from the stream.

22 Claims, 10 Drawing Sheets

| Input Sheath Fluid ||||||||| 
|---|---|---|---|---|---|---|---|---|
| SF | IS | SF | IS | SF | IS | SF | IS | SF |
| Input Sheath Fluid |||||||||

Using Three Actuators on M, W, F

Using Two Actuators on S1, S2

Using One Actuator on S1

Using Two Actuators on M, F

Using Laser Killing or Activation

Using Electrical Killing or Activation

METHOD AND APPARATUS FOR SORTING CELLS

The invention pertains to a flow sorter employing a multi-angular discriminating detection and imaging system, for sorting cells. Another aspect of the invention pertains to a method and apparatus for optical detection and for imaging of objects.

Known imaging systems tend to be azimuthally symmetric, accepting light within a certain range of angles established by the numerical aperture, (NA) of the imaging system. All light coming from the object plane within the NA is ideally transferred to the imaging plane uniformly, in the absence of aberrations or vignetting by optics or apertures which are too small. The reason for this design is that it is desirable to have a reasonably high light collection efficiency (i.e. a high NA) and the angular variations in intensity often do not carry important information.

An exemplary imaging system is a single round lens or a pair of round lenses. For cases where high collection efficiency is desired, such as in imaging systems which are dim, a high NA system is designed by using an optical element which is large compared to the size of the object, and which is close compared to its size. In this way, the lens captures a large fraction of the light. High NA is also important for maximizing resolution and for obtaining a narrow focal depth.

Flow cytometers are devices which use optical scattering and fluorescence to discriminate between cells or other small objects such as fluorescent beads, and to sort them based upon the discriminated optical measurements. As objects stream through a narrow jet, input laser light scatters, impinging on the objects, and incites fluorescence. Scattered and fluorescent light signals are detected at varying angles to characterize and discriminate objects with differing properties.

One difficulty in gender sorting sperm is the very flat shape of sperm, especially bovine sperm. The flat shape, combined with the higher index of refraction of DNA relative to the aqueous environment, causes lensing of light and internal reflection, including fluorescent light which originates in the sperm head. This lensing causes light to be emitted preferentially through the edges of the sperm, with much lower emission through the two flat faces of the sperm head. Thus, detection of light intensity and determination of X or Y chromosomal content of the sperm is dependent upon reliable alignment of the sperm and the ability to view the sperm fluorescence from multiple angles.

Known alignment systems employ a device in which sperm cells are oriented and sprayed into a detection zone by means of a nozzle such as illustrated in Rens et al., U.S. Pat. No. 5,985,216. In such a device, the sorting nozzle has an elliptical cross section for orienting flattened cells. A disadvantage of Rens is that if the flow rate is above about 5000 sperm cells per second, the cells can not be reliably imaged and characterized. A 5000 sperm cells per second sperm flow rate is inefficient and time consuming. A more practical rate for sperm sorting is around 100,000 sperm cells per second or higher.

One type of imaging system used to manipulate small particles is described in U.S. patent application Ser. No. 10/974,976, entitled "SYSTEM AND METHOD FOR MANIPULATING AND PROCESSING NANOMATERIALS USING HOLOGRAPHIC OPTICAL TRAPPING", filed Oct. 28, 2004, and in U.S. patent application Ser. No. 10/934,597, filed Sep. 3, 2004, entitle "MULTIPLE LAMINAR FLOW-BASED PARTICLE AND CELLULAR SEPARATION WITH LASER STEERING", the teachings of both, which are herein incorporated by reference.

SUMMARY OF THE INVENTION

The present invention pertains to a flow sorter employing a multi-angular discriminating detection and imaging system, for sorting cells. One aspect of the invention pertains to a method and apparatus for optical detection and for imaging of objects. In particular, the present invention is directed to a method and apparatus for characterizing and sorting bovine sperm by gender. However, it should be understood that other types of mammalian sperm cells and the like may be sorted by using the present invention.

The present invention is based upon the discovery that a flow sorter for sorting and orienting cells employs a flow channel having an inlet, an outlet, an intermediate detection zone, and optionally, a sorting region. The inlet receives one each of alternating spaced streams of input sheath fluid and a sample stream containing the cells to be sorted between sheath streams. The sheath streams and the sample stream have respective flow rate or pressures in the flow chamber such that the sample stream is constricted thereby forming a relatively narrow sample stream in the detection region whereby the cells are oriented in a selected direction relative to the input light. A detector employing a multi angle or K-Vector imaging setup is focused in the detection zone for discriminating between desired and undesired cells.

DESCRIPTION OF THE INVENTION

Figure 1:
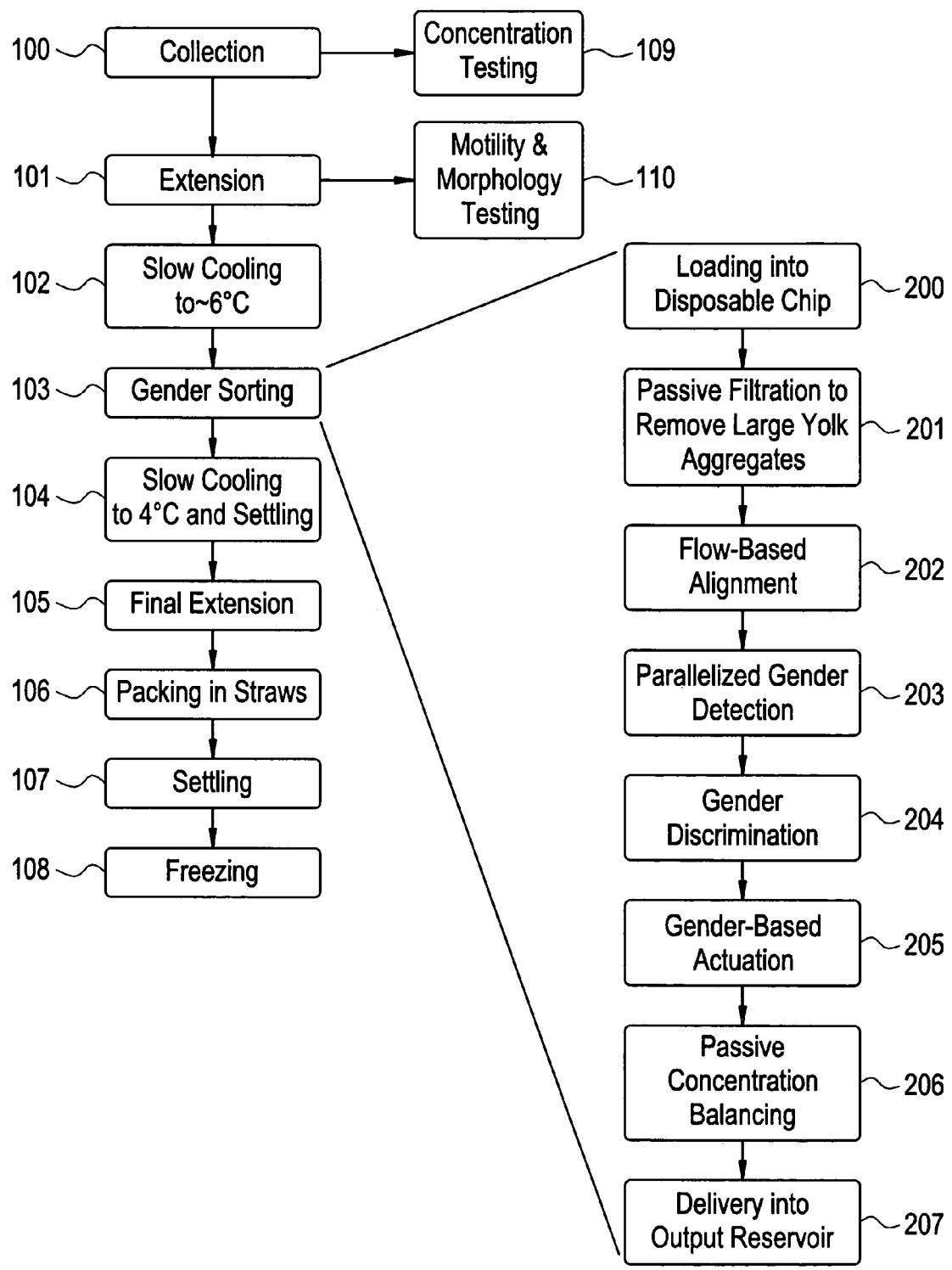
FIG. 1 is a flow diagram of steps for sorting cells which have been dyed with a fluorescent dye.

FIG. 1. illustrates a flow diagram setting forth the steps for characterizing, sorting and processing objects, for cryogenic preservation, particularly bovine sperm cells.

The first stage from collection 100, extension 101, to slow cooling 102, is the subject of various procedures, some of which are novel and others of which are known.

A novel system for preparing cells for sorting is set forth in copending U.S. patent application Serial Number (to be assigned), entitled: "Novel Method For In Vivo Staining of Cells for Identification and Sorting", filed on Feb. 1, 2005, the teachings of which are incorporated herein by reference.

The steps include loading a sample into a disposable chip 200; filtering the sample to remove large aggregate material 201, such as yolk aggregates; employing flow based alignment 202 as set forth hereinafter; employing parallelized gender detection 203, discrimination (i.e., gender discrimination 204) and actuation (i.e., gender actuation 205) steps; passive concentration and balancing 206, and delivery to an output reservoir 207. The method may also optionally eliminate some steps and include a discrimination and killing step for removing unwanted live sperm.

The gender sorting steps 103 which includes the above, are then followed by slow cooling to 4° C. and settling 104; final extension 105; packing in straws 106; settling 107 and freezing 108 steps.

Figure 2:
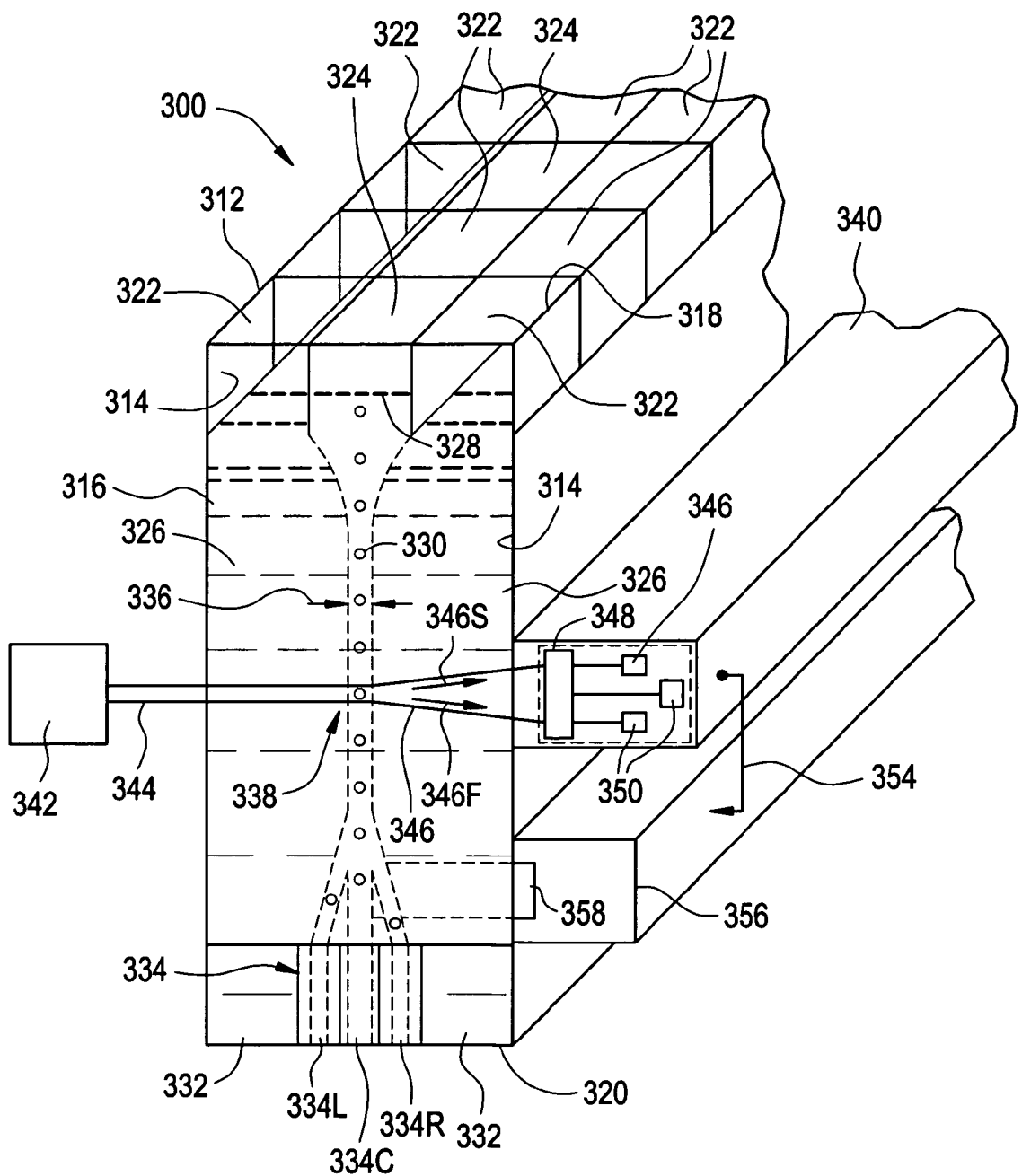
FIG. 2 is a perspective schematic illustration of a flow device or cartridge according to the invention.
Figure 3:
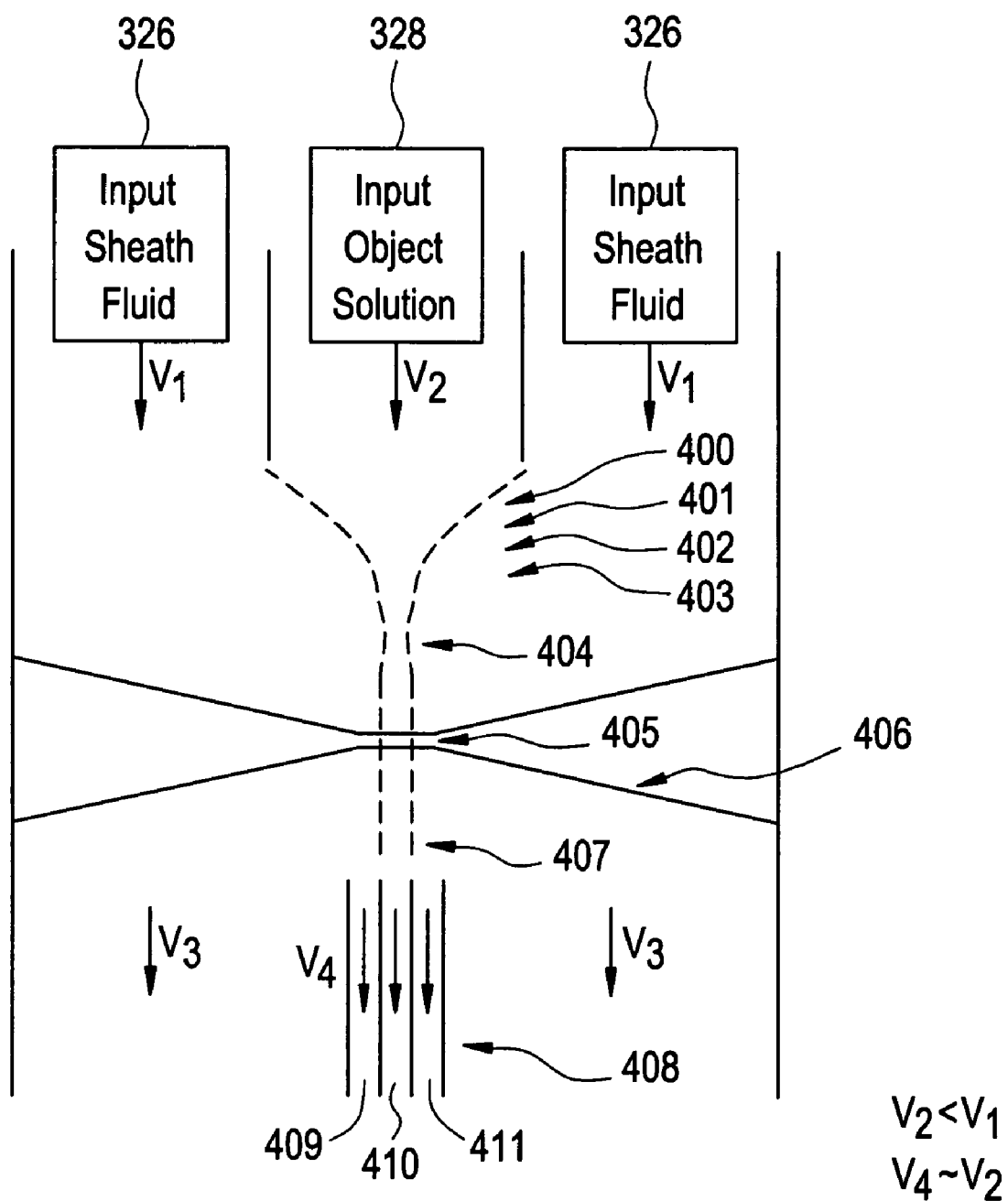
FIG. 3 is a schematic illustration of a single channel flow device for sorting.

FIGS. 2-3 illustrate in various forms a flow cytometer 300 according to the invention. The device may be a single channel system. However, the invention is well suited for multichannel applications, particularly in sperm cell sorting applications, where large numbers of sperm cells must be sorted in a reasonable amount of time.

In FIGS. 2-3, the device 300 comprises a body or flow chamber 312 formed of a pair of confronting walls 314 and end walls 316 (only one of which is shown in FIG. 1), an open top or input 318 and open bottom or output 320.

The input 318 is divided into three sections including outboard inputs 322 and central or sample input 324. The outboard inputs 322 are for receiving a sheath fluid 326 therein and the central input 324 is for receiving a sample fluid 328 containing a liquid medium and cells 330 dispersed therein.

The output 320 has outboard output sections 332 and central sample collection channels, namely left output sample channel 334L, central output sample channel 334C and right output sample channel 334R. Channel 334L is for a first sorted sample, 334C is for a second sorted sample, and 334L is for yet another sorted sample.

Sheath fluid 326 is input at outboard inputs 322 at a selected flow rate. Sample fluid 326 is introduced in central input 324 at a selected flow rate or pressure relative to the sheath flow rate or pressure such that the sheath fluids compress and constrict the sample flow to a relatively narrow sample flow path 336 as shown. In an exemplary embodiment, the width of the sample flow path 336 is about 10% or less of the width of the sample fluid at the central input 324, e.g. about 50 microns.

The cells 330 are circular but flattened. As a result, constriction of the sample fluid causes the cells 330 to orient themselves so that their flat sides are roughly parallel to the confronting walls 314. The intensity of light radiated by a cell is different at different orientations. So to compare the intensity of two or more cells, they must have the same orientation. Thus, aligned cells reduce noise or systematic error caused by having anisotropic light emitter at random orientations.

Alternating inputs of sheath fluid 326 and input sample or object solution 328 (see FIG. 3) enter the system, creating a small amount of constriction (relative to the constriction in the orthogonal direction) 401, which causes shear and the shear flow aligns the cells 400. This alternating flow pattern is squeezed more severely between two long input sheath fluid flows, which achieves the necessary alignment. This arrangement may be combined with detection hereinafter to provide a parallel system where multiple flows may be interrogated.

Specifically, the constricting flow moves objects into the focal plane 402, and accelerates movement through the detection region 403. The curve 404 in the system shows the fluid boundary 404, and the detection region 405 allows for characterization. The light cone 406 allows for interrogation, and the default stream position 407 can be steered between multiple outlets.

By varying the flow rate through the three output channels 409-411, cells or other objects in the solution can be sorted into one of multiple output streams. The actuation may be done in various ways, as enumerated above. High-speed flow switching may be performed by piezo devices which may be intrinsic to the machine, or intrinsic to the disposable flow channel cartridge. Flow switching region 408 controls the precise flow rate, which varies over time to switch between output channels 409-411 (where V2<V1, and V4~v2).

The detector 340 (FIG. 2) comprises a laser 342 or other suitable source producing an output beam 344 directed towards the sample flow path 336 in a detection zone 338 intermediate the input and output. The beam 344 impinges on the cell 330 in the detection zone 338 and scatters forming an output beam 346. The cell contains a fluophor and thus produces fluorescent light as well which is contained in the output beam 346. Respective scattered and fluorescent components 346S, 346F of the output beam 346 are input to an optical detector containing an optical system 348 and an electronic detector system 350. The optical system and electronic detector system are discussed hereinafter.

The output beam 346 carries information to the detector 340 which discriminates among the cells 330 and produces an output 354 to a sorter 356. The sorter 356 controls drivers 358 in operative relationship with the output channels 334 in order to vary the relative flow rates such that the each cell 330 is sorted into a proper channel. Alternatively, the cells may be sorted as wanted or unwanted, and the wanted cells may be collected and the unwanted cells may be destroyed.

Figures 4, 4A:
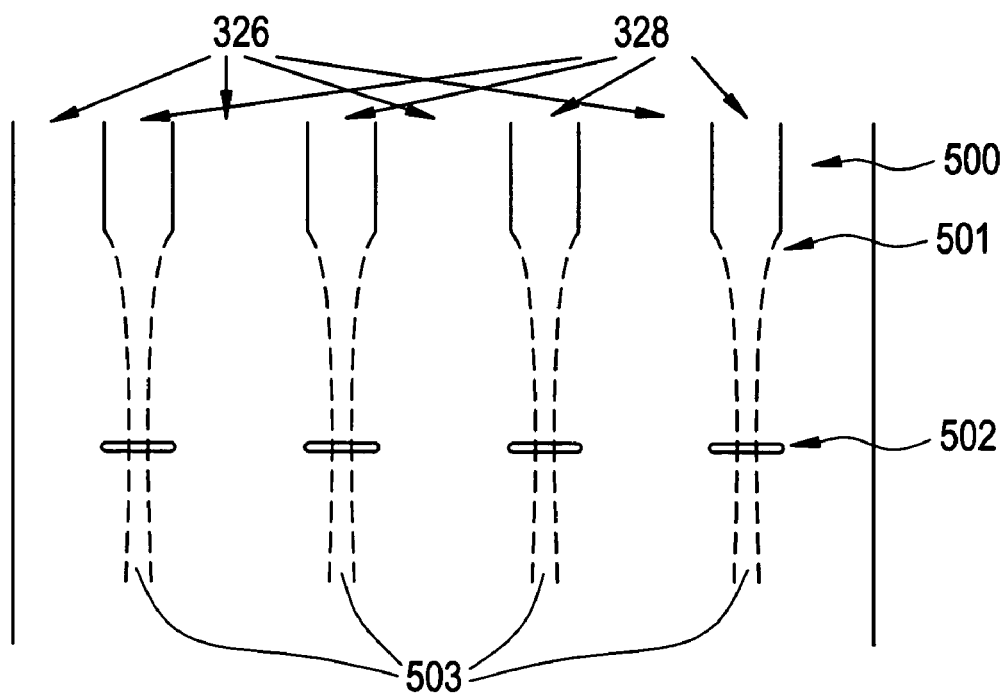
FIG. 4 is a side-view of a multichannel flow device for sorting.
FIG. 4A is a top plan (edge) view, facing the inputs, of the multichannel system shown in FIG. 4.

FIG. 3 shows a single channel system having only two sheath flows 326 and one sample flow 328. FIG. 4 shows a multi-channel system with four sample flows 328 and shared sheath flows 326. FIG. 4A shows the flow chamber and flow paths in top plan.

FIGS. 4-4A show one possible way of parallelizing the design to have many parallel streams 500 of input solution. Flow may constrict both in the plane and normal of the plane. However, for cases where alignment of cells is necessary, such as with bovine sperm, shear along the direction of the incoming light must be much larger to guarantee alignment normal to the incoming light. The optical investigation region 502 is where laser scattering and fluorescence takes place.

In the example, each sheath has a dedicated lens system, multiple PMT elements each of which is dedicated to a corresponding stream. It should be understood that the system may have one lens detector system for all channels and one laser optic system for all channels as well. There are multiple possible output channels 503 for each flow stream.

Figure 5:
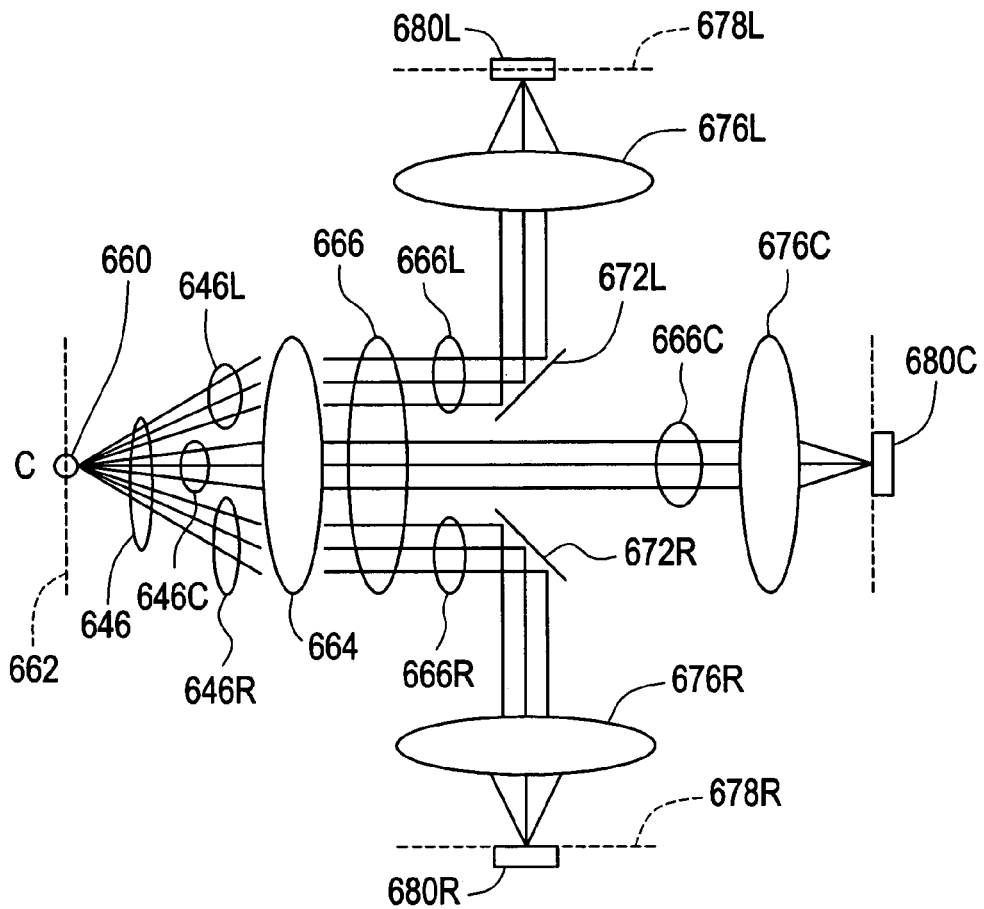
FIG. 5 is a schematic representation of a single channel sensor for sensing scattered light (i.e., optical system for K-vector imaging).

A simplified plan view of the optical system of the detector 640 is shown in FIG. 5. A sample 660 lies in an object plane 662. In this illustration output beam or, light rays 646 emanate from the sample 660 as beamlets 646C, 646L, 646R. The beamlets 646C represent centrally clustered beams near the central optical axis C; and beamlets 646L and 646R are clustered to the left and right of the central axis C. The beamlets provide different views of the sample 660. A collection lens 664 (which may be an objective lens from a microscope) is positioned a distance from the object plane 662 which is equal to the effective focal length (EFL) of the lens. The lens 664 may be a compound lens if desired, but for simplicity it is described it as a single lens with an EFL. By positioning lens 664 thus, light 646 from the object exits the collection lens 664 is collimated as beamlets 666 likewise divided as 666R, 666C, 666L as shown. This creates an infinity space in the imaging system. While the present invention does not require this infinity space, it is a convenient arrangement. The lateral positioning of each collimated light ray is determined predominantly by its angle coming from the object plane. Beamlets 666L, 666R and 666C follow respective beamlets 6421, 642R and 642C.

Figure 5A:
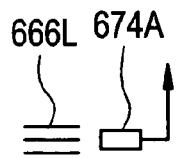
FIGS. 5A-5D illustrate alternative optical elements employed in the arrangement of FIG. 5.
Figure 5B:
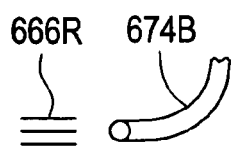
Figure 5C:
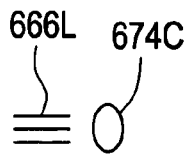
Figure 5D:
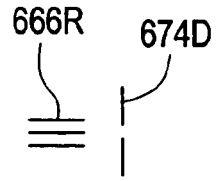

Central light beamlets 666C exit lens 664 along central axis C to focusing lens 676C which focuses the light on forward image plane 678C. Mirrors 672L, 672R separate off-axis beamlets 666L and 666R exiting the collecting lens 664. Note that this may also be done with the placement of detector 674A (FIG. 5A0 or optical fiber 674B (FIG. 5B) in this region which are small compared to the size of the beam in this space. Note also that additional optical elements may be inserted in this space, such as additional lenses 674C (FIG. 5C) or a pinhole 674D (FIG. 5D) to constrain the range of angles of light coming out of the collecting lens 664, or to control (restart or expand) the focal depth from which light is collected as in confocal microscopy measurements. In some circumstances, a pair of additional lenses, with a pinhole, may be used. In other cases, a mask with controllable size shape, or position may be used to control the light reaching a given detector.

The light from beamlets 666L is deflected by mirror 672L to left focusing lens 676L; and from beamlet 666R light is directed by mirror 672R to lens 676R and right image plane 678R. Light detectors 680L, 680R and 680C may be located in respective image focal planes 678L, 678R and 670C to detect the respective images. These light detectors may be CCD, photo diodes, photomultiplier tubes, multi-anode photomultiplier tubes, or other sensors.

Figure 6:
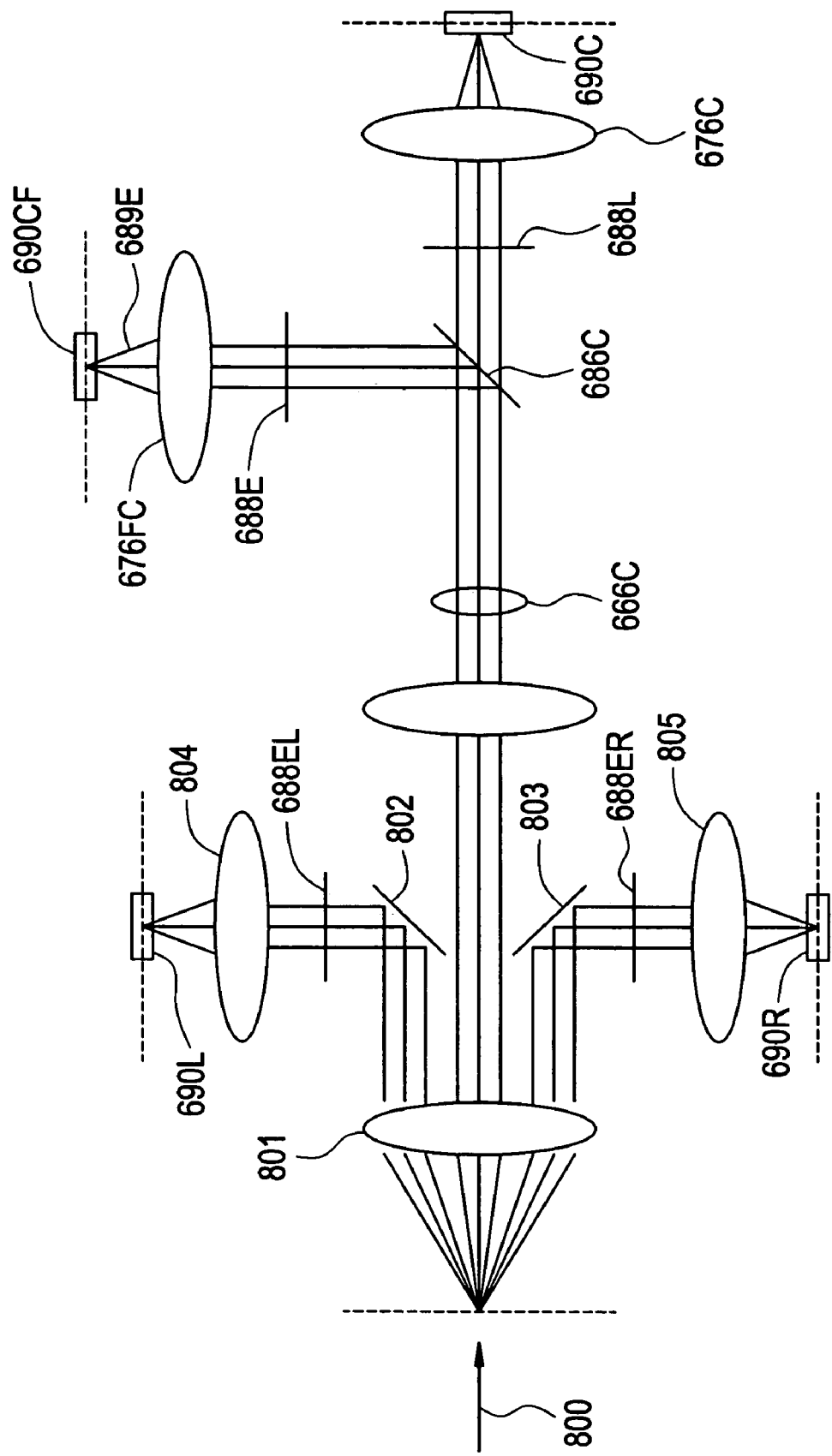
FIG. 6 is a schematic representation of a single channel sensor for detecting fluorescent and scattered light using K-vector imaging.

In many cases, it is desirable to collect both scattered light and fluorescent light, where at least one of the images or detections made require a reduced range of ray angles from the sample. FIG. 6 illustrates how this may be done, using the K Vector Imaging setup as described above, but with filters and additional beam splitters as necessary. Similar elements have the same reference numerals.

In FIG. 6, illumination and excitation light 800 passes through collecting lens 801, and is reflected by mirrors 802, 803 through emission filters 688EL, 688ER to focusing lenses 804, 805 and to photo detectors 690L, 690R, respectively, which form the left and right fluorescent image planes.

The beamsplitter in 686C redirects light in the central field 666C through an emission filter 688E to focusing lens 676FC. The output 689E of emission filter 688E corresponds to fluorescence emission from the cell. Laser line filter 688L in the central optical axis filters scattered laser light to lens 676C and photo detector 690C, where is formed he forward scattered image plane.

Figure 7:
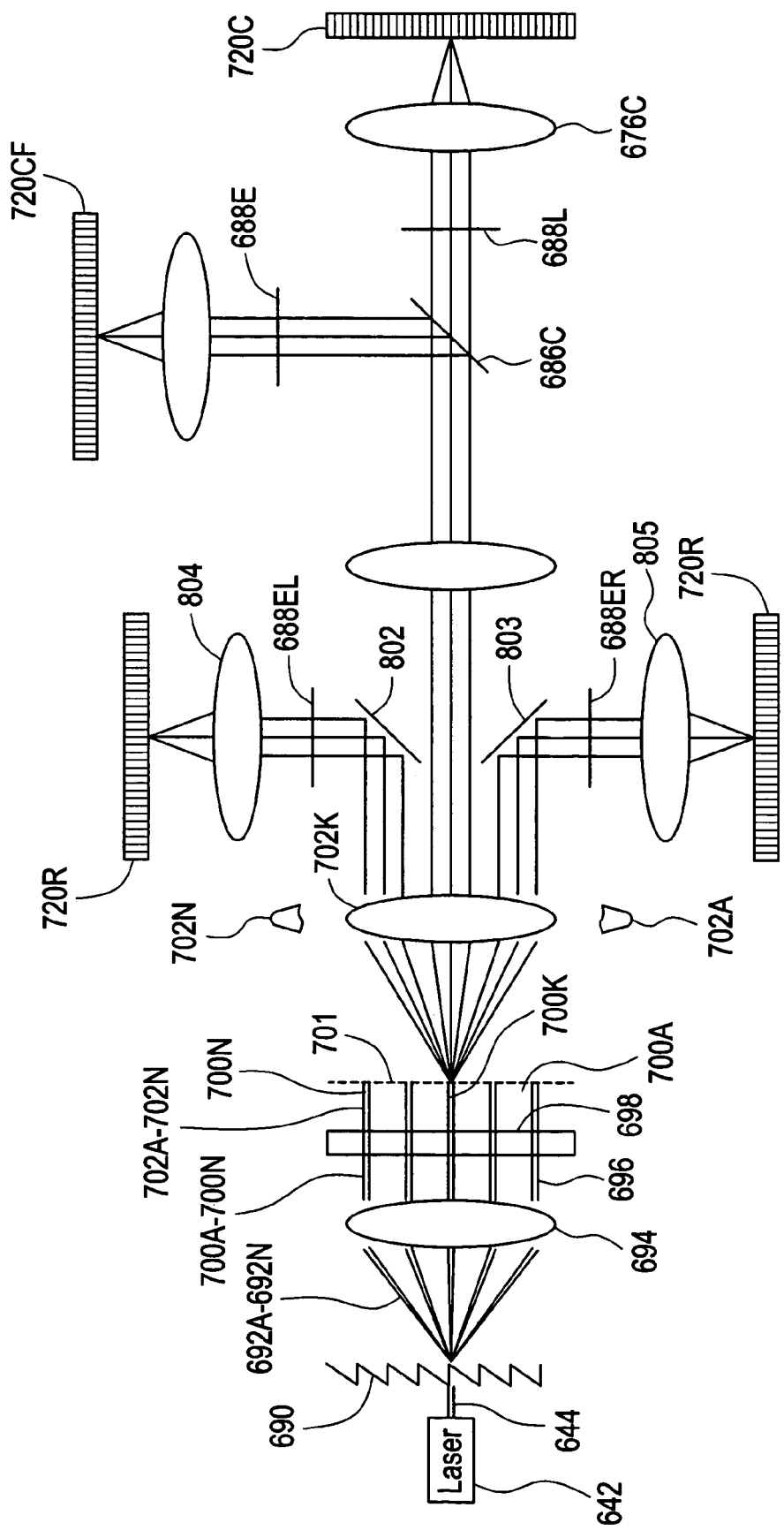
FIG. 7 is a multichannel channel device for K-vector imaging with excitation and detection of scattered and fluorescent light.

To improve the throughput and overall capabilities of a device, parallelization is desired. FIG. 7 shows how this is accomplished. Laser 642 produces input laser beam 644, which excites fluorescence, is broken up into N multiple beams by beamsplitter 690 (e.g., diffraction grating or hologram). Beams 692A and 692N fan out and each are directed to the detection zone of a corresponding sample sheath (see FIG. 4). The beamlets 692A-692N are collimated into parallel beams by the collimating lens 694. The output 696 of the collimating lens 694, is directed through cylindrical lens 698 which focuses individual beams 700A-700N onto the sample streams in the object plane 701. As shown, (FIG. 4) the input stream is broken up into many streams. Light from one or all beamlets 700A-700N in the example shown and sample streams enters collecting lens 702K and is handled as described in FIG. 6 above. Here, however, detector array devices (such as multi-anode PMTs) device 720 (720C, 720R, 720L, 720CF . . . ) one for each group of detection beams are used. Detection is best accomplished not by placing a single detector in each imaging position, but by using array detectors, such as a 32-element linear PMT array 720.

The throughput of a system which images or make measurements on many objects will depend, in part, upon the number of detectors and their speed. For many applications, a single detector such as photomultiplier tube (PMT) is used in each image plane. This is suitable for cases where objects pass through the object plane in a single-file line.

Figure 8:
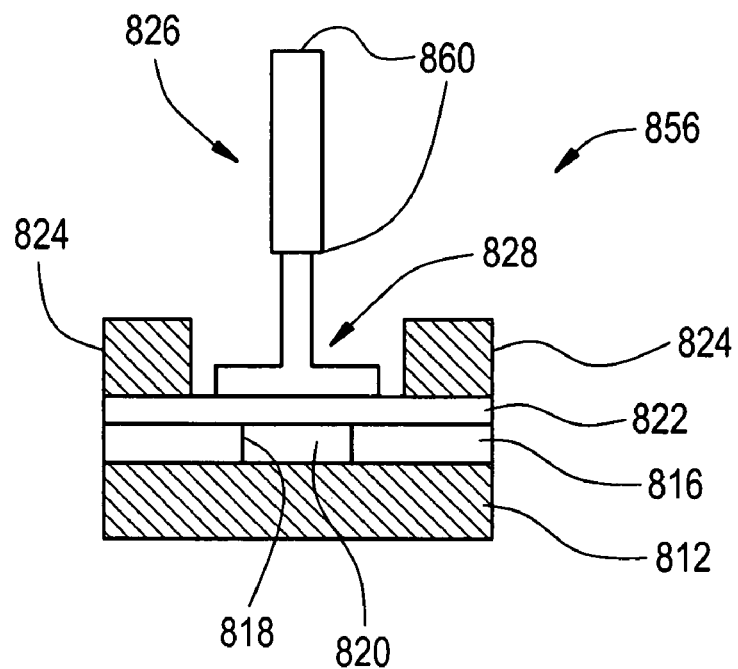
FIG. 8 is a schematic representation of an external actuator adjusting flow speeds in a channel or device for sorting cells.

The sorter 856 is hereinafter described in detail. A single channel sorter is shown in FIG. 8. The sorter 856 comprises a structural member 812; a channel defining layer 816 formed with a slot 818 defining a flow channel 820; a flexible membrane layer 822 atop the channel defining layer 816, and a structural member 824 completing the arrangement. Piezoelectric or another type actuator 826 is coupled to a controller 828. A piston 860 driven by actuator 826 engaged flexible membrane 822 opposite the flow channel 820 to change the flow pattern within the channel in accordance with the voltage supply to the piezo-electric. A plurality of such structures may be miniaturized so as to be located in the actuator window whereby multiple streams of samples may be sorted.

The one or more actuators 826 may include: a piezoelectric transducer for converting electrical signals into mechanical actuation of the flow rates; a thermal heater for heating a region to quickly expand a fluid, material, or bubble; a thermal bubble generation for creation of a bubble to reduce the flow of the solution; a capacitive motion device for a membrane; an optical device for heating or moving material, wall, membrane, bubble, or other material or object to impact the flow velocity into one or more of the output channels 934. The actuation may be intrinsic to the device or may be externally applied. For example, the actuator 826 and piston 860 may be external equipment, separate from the disposable flow device 856 (i.e., disposable chip with non-disposable/external actuator).

Figure 9:
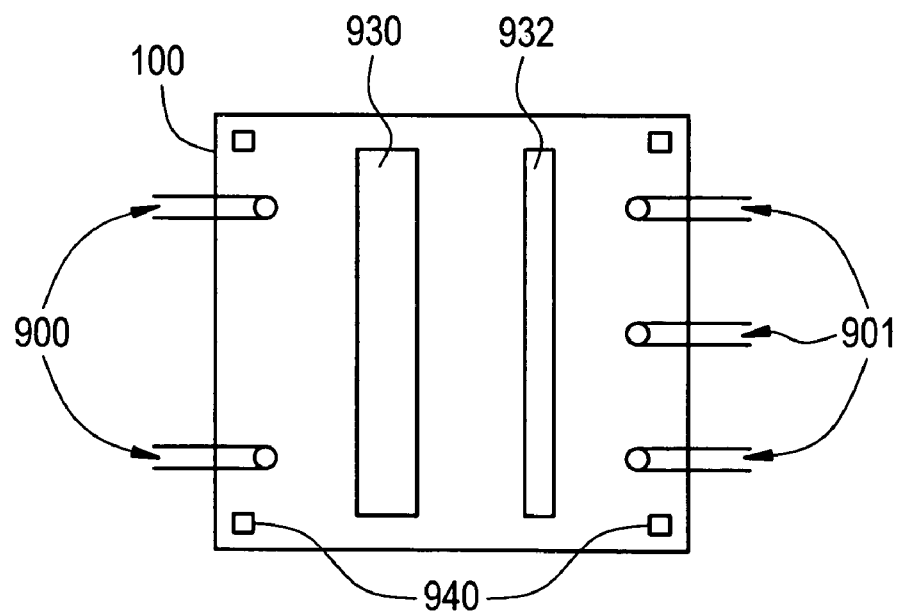
FIG. 9 is a schematic representation of a top view of a multichannel device or cartridge for detecting and sorting cells.

FIG. 9 illustrates the parallel arrangement of multiple channels in which input channels 900 feed the sheath streams to the flow channels and output channels 901 receive the various sorted sperm cells. Window 930 is provided for coupling interrogation light to each of the parallel detector sample channels. Sorter window 932 receives a plurality of actuators and disposable sorter elements. Chip registration pins of the device 100 are designated as 940.

Figure 10A:
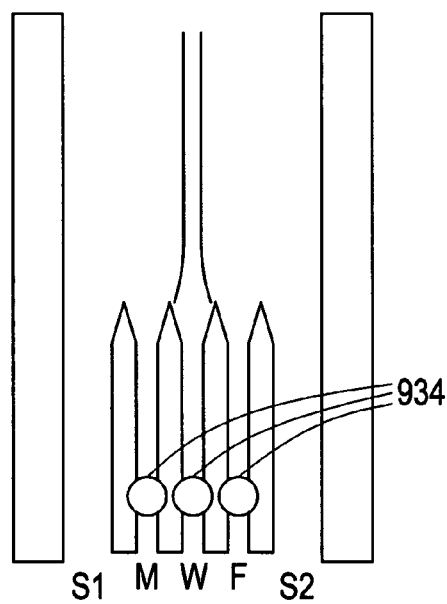
FIGS. 10A-10D show various alternative ways of steering cells using three actuators on M, W, F (FIG. 10A), two actuators on S1, S2 (FIG. 10B), one actuator on S1 (FIG. 10C), and two actuators on M, F (FIG. 10D).
Figure 10B:
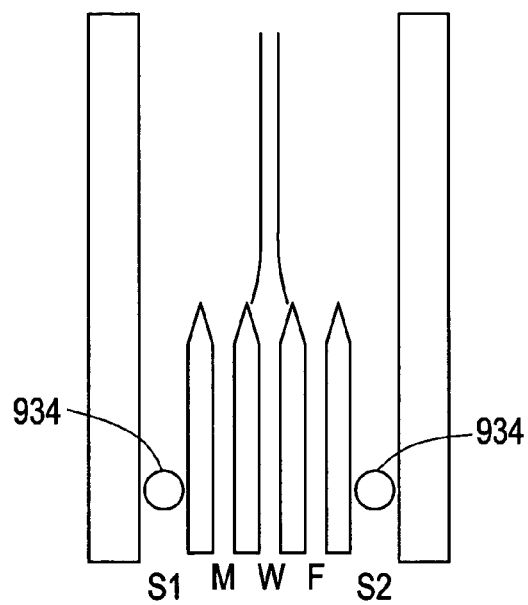
Figure 10C:
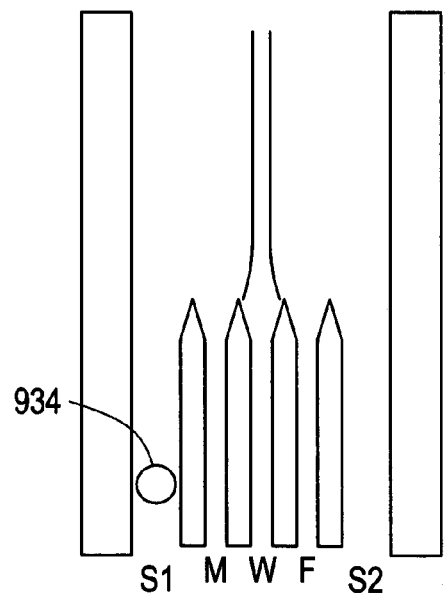
Figure 10D:
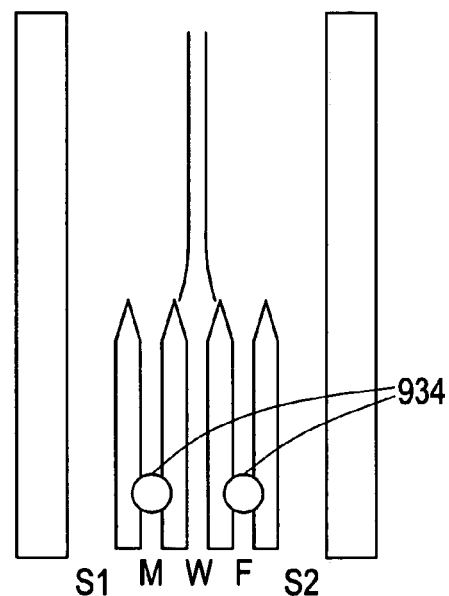

FIGS. 10A-10R illustrate alternative embodiments for steering cells, employing a variety of actuators 934 in a flow device for sorting sperm. In each case, one or more actuators are used, where each actuator could be based off of piezoelectric devices (intrinsic or extrinsic to the cartridge), capacitive actuators, thermal expansion, or other technologies as described in the prior disclosures. In most cases, at least two actuators 934 are desired, and possibly more than two actuators, to control which exit channel 936 a particular cell or object goes into. The actuators allow one to control and vary the flows at very high rates. Only minor perturbations to the flow are necessary to cause a stream to temporarily move from one exit to another.

Figure 11A:
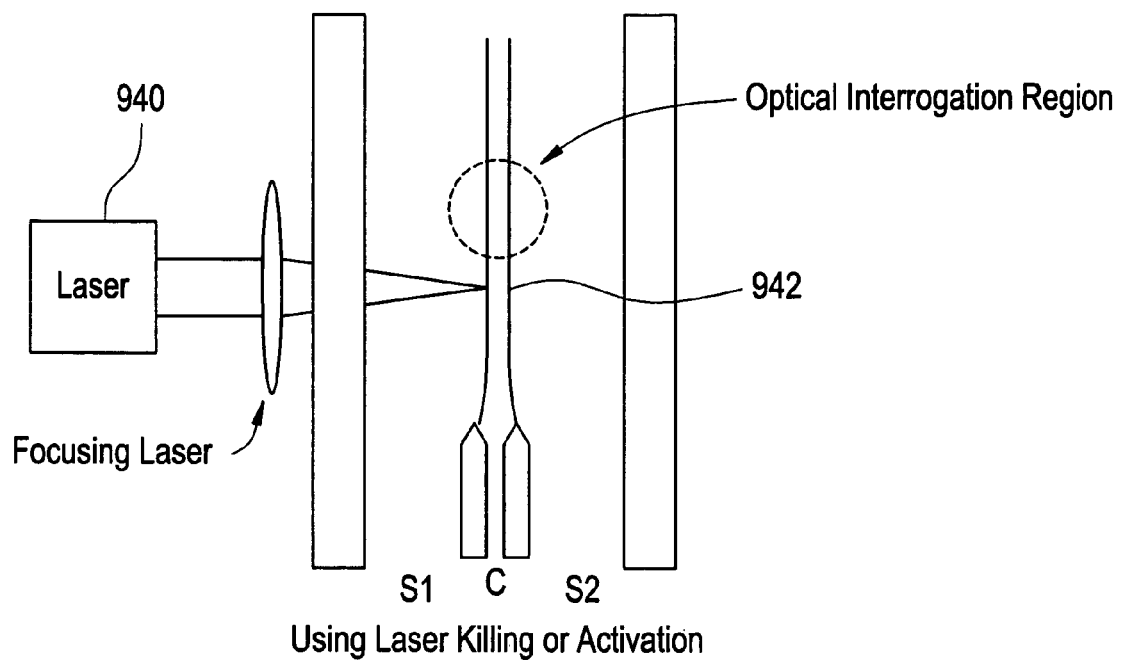
FIGS. 11A-11B show various alternative ways of killing cells by laser killing or activation (FIG. 11A), and electrical killing or activation (FIG. 11B).
Figure 11B:
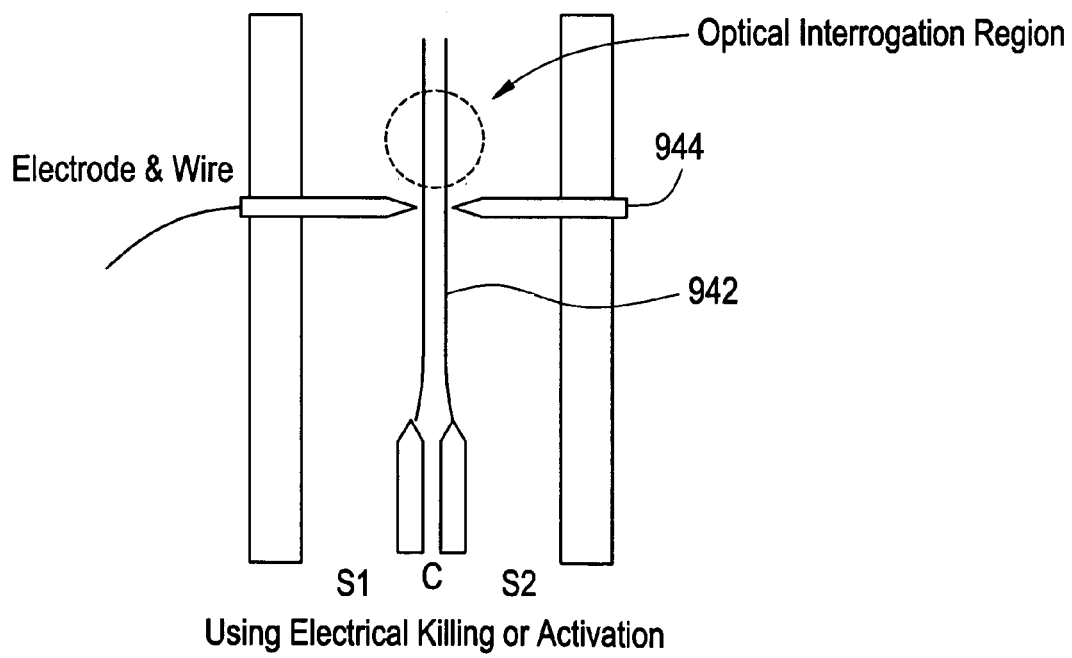

FIGS. 11A-11B show examples of killing or activation setups without sorting for achieving a desirable result. In the FIG. 11A, a laser 940 impinges the object/sperm stream 942. This laser is controlled to only impinge lethal energy on certain sperm or objects depending upon the result of the interrogation. For example, this laser may kill certain sperm or other cells as desired. For example, it may kill all sperm of a given or uncertain gender. Alternately, the laser may not directly kill the cells but may otherwise "activate" them. For example, it could activate some chemical which has been previously introduced into the sperm, having the overall result of killing them or otherwise impairing fertilization. In more general applications, activation may have a much broader range of activities.

FIG. 11B shows killing or activation using lethal electrical pulses, introduced through electrodes 944 which are inserted into the flow in order to locally access the central stream 942. As with the laser solution, the electrodes can be quickly pulsed on or off depending upon the result of the interrogation.

Steering may also be achieved optically where the cells are manipulated by an optical trapping apparatus. Alternatively, the actuation process may be electroporation of the cells, which may be lethal or have other effect on the cells.

The following technique aligns sperm cells using squeezing flow:

Three flows were fed into a flow chip using a peristaltic pump. Each flows were kept in laminar regime so that each flow does not mix each other. The stream containing sperms flows between top and bottom streams which are waters. While the velocity of top and bottom flow is kept same, by changing the ratio of those to the sperm flow, we could see the squeezing of sperm flow.

|      | sperm orientation (%) angle from flow direction (degree) | | | |
|------|------|------|------|------|
| Re   | <3   | <15  | <45  | >45  |
| .066 | 51.35 | 29.73 | 13.51 | 5.41 |
| 1.35 | 61.11 | 14.81 | 22.22 | 1.85 |
| 2.13 | 66.67 | 16.67 | 16.67 | 0    |

It is expected that the squeezed flow helps the sperm oriented to the flow direction.

Images of the sperm in flow were taken using a CCD camera equipped on our microscope.

Above table shows the degree of sperm orientation in the flow where Re is the Reynolds number defined as $Dur/m$ where D is diameter of flow channel, U is the speed, r is density of fluid and m is the viscosity.

Re indicates whether the flow is laminar or not, even though Re below 1000 is considered laminar flow, in some applications, very small Re such as below 1 is required.

As the speed of sperm flow increases the Re in the channel inlet increases but still remains in laminar region indicating the flow stream is not disturbed in our experimental region.

The orientation of sperm was quantified by numbering of those as function of degree alignment of sperm head to flow direction.

In the experiment range, about 80% of sperms imaged were oriented in less than 15 degree to flow direction.

Better alignment to flow direction was shown at higher speed but more disturbed sperms were also found.

The results shows that the system could align sperms using this technique.

It should be understood that temperature control of the sheath fluid and sample fluid can be employed to prolong sperm life. In an exemplary, embodiment the temperature of the fluids in the flow device may be maintained around 2-10° C. in order immobilize the sperm cells and thereby extend their lifetime.

The invention claimed is:

1. A flow apparatus for orienting, examining and selectively operating on cells comprising:
   a flow chamber having confronting walls and an input region, a detector region, and a selective operation region;
   wherein said flow chamber includes a plurality of inlets into said input region, each of said inlets adapted to receive an input stream of fluid;
   wherein said input streams of fluid are one of an input sheath fluid or an input sample fluid containing cells to be processed;
   wherein said input sample fluid is in a contiguous relationship on all available sides with said input sheath fluid from at least said input region through to said selective operation region;
   wherein at least one of flow rates or pressures of said input sheath fluids are chosen such that said input sample fluid is constricted in two orthogonal directions, thereby allowing said input sample fluid to form a relatively narrow stream in at least the detector region, thereby causing the cells to be flattened and aligned such that flat sides of the cells are oriented parallel to the confronting walls;
   a sorter disposed in said selective operation region, which varies flow rates of the cells in order to sort desired cells from the stream; and
   a plurality of spaced apart regions or channels at least one of which receives the desired cells.

2. The apparatus of claim 1 wherein in the selective operation region, desired cells are separated from undesired cells by killing the undesired cells.

3. The flow apparatus of claim 2, wherein the cell killing is accomplished through at least one of laser killing, electrical pulse activation electrophoration, or activation of cells.

4. The apparatus of claim 1 wherein the sample fluid includes cells or particles suspended therein.

5. The apparatus of claim 1 further comprising:
   a downstream outlet disposed downstream from the selective operation region.

6. The apparatus of claim 1 further comprising:
a detector disposed in the detector region;
wherein the detector comprises an optical source for optically illuminating the cells in the detection region with an input light beam.

7. The apparatus of claim 6 wherein the detector in the detector region detects desired cells.

8. The apparatus of claim 7 wherein the sorter includes a pressure transducer responsive to the detector for selectively applying pressure to one or more of said regions or channels in order to steer the desired cells into a first sorting region and undesired cells into a second sorting region.

9. The apparatus of claim 6 wherein the cells are responsive to produce output light in response to the input light beam, and the detector comprises an optical detector responsive to light produced by the cells.

10. The apparatus of claim 9 wherein the output light comprises at least one of light scattered from the cells, and fluorescent light produced by the cells.

11. The apparatus of claim 6 wherein the detector comprises an optical train for receiving output light from the cells including a first optical element for collecting the output light and producing collected light beamlets thereof, said beamlets representing various angular images of each of the cells produced in accordance with interaction of each of the cells with an input light beam.

12. The apparatus of claim 11 wherein the detector further comprises an optical detector in alignment with a central optical axis of the optical train for directing selected on-axis beamlets aligned with the central axis to corresponding optical detectors.

13. The apparatus of claim 12 wherein the detector further comprises at least one off-axis optical detector having a corresponding off-axis optical path for detecting off-axis beamlets having optical paths oriented off-axis from the central optical axis.

14. The apparatus of claim 12 further comprising:
an optical splitter in the optical path of the at least one off-axis optical detector directing selected beamlets from the collected light beamlets to the corresponding off-axis detector.

15. The apparatus of claim 12 wherein the collected light beamlets includes scattered light and fluorescent light, and the detector further comprises optical filters for filtering at least one of the scattered light and the fluorescent light from the collected light.

16. The apparatus of claim 1
wherein the sorter comprises:
a flow channel for each type of cell, and
a drive member coupled to a flow channel containing the sample fluid, for modifying the fluid flow rate at selected locations in the sample fluid for steering the cells to selected ones of the channels.

17. The apparatus of claim 16 wherein the drive member comprises a pressure transducer for the varying pressure applied to the flow channel.

18. The apparatus of claim 16 wherein the drive member comprises at least one of a piezo-electric transducer; a thermal heating unit; a capacitive membrane and an optical heater.

19. The flow apparatus of claim 1, wherein the cells are sperm cells.

20. The flow apparatus of claim 1, wherein the cells are sperm cells, and the selective operation is gender discrimination of the sperm cells.

21. The flow apparatus of claim 1, wherein the orientation and the selective operation of the cells is for selective property discrimination.

22. The flow apparatus of claim 1, wherein said input sample fluids in said input regions, detector regions, and selective operation regions, are parallelized within the flow chamber.

* * * * *